US006207863B1

(12) United States Patent
Berrier et al.

(10) Patent No.: US 6,207,863 B1
(45) Date of Patent: Mar. 27, 2001

(54) SYNTHESIS OF HALOFORMIMINE COMPOUNDS

(75) Inventors: John Vincent Berrier, Mount Laurel, NJ (US); Ashutosh Sumantrai Umarvadia, Horsham, PA (US)

(73) Assignee: Rohm and Haas Company, Philadelphia, PA (US)

(*) Notice: Subject to any disclaimer, the term of this patent is extended or adjusted under 35 U.S.C. 154(b) by 0 days.

(21) Appl. No.: 09/318,473

(22) Filed: May 25, 1999

Related U.S. Application Data

(60) Provisional application No. 60/096,054, filed on Aug. 11, 1998.

(51) Int. Cl.[7] ................................................. C07C 249/00
(52) U.S. Cl. .......................... 564/253; 564/254; 564/256; 564/258; 564/259; 564/268
(58) Field of Search ..................................... 564/253, 254, 564/256, 258, 259, 268

(56) References Cited

U.S. PATENT DOCUMENTS

| 4,692,538 | 9/1987 | Vyas et al. ................................. 558/6 |
| 4,879,314 | 11/1989 | Hsu ........................................ 514/640 |

FOREIGN PATENT DOCUMENTS 7-173004   7/1996   (JP).

OTHER PUBLICATIONS

John C. Rohloff, et al., *Tetrahedron Letters*, vol. 33 (22), pp. 3113–3116 (1992).
De Paolini, I., *Gazzetta Chimica Italiana*, vol. 60, pp. 700–704 (1930) (in Italian).
"Methods for the Stereoselective Cis Cyanohydroxylation and Carboxyhydroxylation and Carboxyhydroxylation of Olefins", Alan P. Kozikowski and Maciej Adamczyk; J. Org. Chem. 1983, 48, pp. 366–372.
Abstract—"A Short, Efficient Total Synthesis of (±) Acivicin And (±) Bromo–Acivicin", D. M. Vyas, Y. Chiang and T. W. Doyle; Tetrahedron Letters, vol. 25, No. 5, pp. 487–490, 1984.

*Primary Examiner*—Porfirio Nazario-Gonzalez
(74) *Attorney, Agent, or Firm*—S. Matthew Cairns; Kenneth Crimaldi

(57) ABSTRACT

Disclosed is an improved method for the preparation of highly pure haloformimine compounds in high yields by reacting a formimine compound in a solvent with a halogenating agent while maintaining the pH of the halogenation reaction in the range of 2 to 5. The pH of the reaction may be maintained by a variety of means, such as by the addition of a base.

9 Claims, No Drawings

SYNTHESIS OF HALOFORMIMINE COMPOUNDS

This application claims benefit to U.S. provisional 60/096,054 filed Aug. 11, 1998.

BACKGROUND OF THE INVENTION

This invention relates to a method for preparing haloformimine compounds. In particular, the present invention relates to an improved process for halogenation of formimine compounds.

Haloformimine compounds are a commercially important class of organic compounds. Haloformimines are useful as intermediates in the synthesis of a wide variety of organic compounds, such as microbicides, agricultural pesticides and pharmaceutical agents, such as antitumor agents. Certain haloformimines are also known as industrial bactericides.

Haloformimine compounds are typically prepared by reacting a carbonyl compound, such as glyoxylic acid, with an iminating agent, such as hydroxylamine, to form a formimine, followed by the addition of a base to the reaction mixture prior to reacting the formimine with a halogenating agent. For example, U.S. Pat. No. 4,879,314 (Hsu) discloses methods of preparing dihalooformaldoximes that require the addition of sodium bicarbonate to glyoxylic acid oxime before the halogenation step. The yield of dibromoformaldoxime by this method is only 46%. There is no discussion of maintaining the reaction at a specific pH during the halogenation step.

Such methods of preparing haloformimines typically result in low yields and the presence of significant levels of by-products. Much cost and effort must then be spent to purify the resulting haloformimine compound.

There is therefore a continuing need for a method of preparing haloformimine compounds that provides high yields and produces very low amounts of by-products.

SUMMARY OF THE INVENTION

The present invention is directed to the surprising discovery that maintaining a pH between 2 and 5 during the halogenation of formimines greatly increases the yields of haloformimines and greatly decreases the rate of by-product formation.

The present invention is directed to a process for preparing haloformimine compounds of the formula

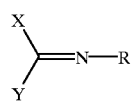

(I)

wherein: X, $X^1$=halo; Y=halo, $CO_2R^1$, $CX^1$(=NR), $C(O)NR^{10}R^{11}$; R=$OR^2$, $NR^3R^4$, N=$CR^5R^6$; $R^2$=H, $C(O)R^7$, $(C_1-C_{18})$alkyl, substituted $(C_1-C_{18})$alkyl, $(C_7-C_{10})$aralkyl, substituted $(C_7-C_{10})$aralkyl, phenyl, substituted phenyl; $R^3$ and $R^4$ are independently selected from: $(C_1-C_8)$alkyl, substituted $(C_1-C_{18})$alkyl, $(C_7-C_{10})$aralkyl, substituted $(C_7-C_{10})$aralkyl, phenyl, substituted phenyl; $R^5$ and $R^6$ are independently selected from: H, halo, $CO_2R^1$, $(C_1-C_{18})$alkyl, substituted $(C_1-C_{18})$alkyl, $(C_7-C_{10})$aralkyl, substituted $(C_7-C_{10})$aralkyl, phenyl, substituted phenyl; $R^7$= $(C_1-C_{18})$alkyl, substituted $(C_1-C_{18})$alkyl, $(C_7-C_{10})$aralkyl, substituted $(C_7-C_{10})$aralkyl, phenyl, substituted phenyl, $NR^8R^9$; and $R^1$, $R^8$, $R^9$, $R^{10}$ and $R^{11}$ are independently selected from: H, $(C_1-C_{18})$alkyl, substituted $(C_1-C_{18})$alkyl, $(C_7-C_{10})$aralkyl, substituted $(C_7-C_{10})$aralkyl, phenyl, substituted phenyl; wherein the process comprises combining a formimine compound with a solvent and sufficient base to provide a mixture having a pH in the range of 2 to 5, followed by reacting said formimine mixture with a halogenating agent to produce a haloformimine compound, while maintaining the pH of the mixture in the range of 2 to 5.

The present invention is also directed to haloformimine compounds prepared according to the process described above.

DETAILED DESCRIPTION OF THE INVENTION

As used throughout the specification, the following terms shall have the following meanings, unless the context clearly indicates otherwise.

"Alkyl" refers to straight chain, branched or cyclic carbon chain, or any combination thereof "Halo" and "halogen" refer to fluorine, chlorine, bromine and iodine. "Substituted phenyl" means one or more of the hydrogens on the aromatic ring are replaced by another substituent, such as cyano, hydroxy, $(C_1-C_4)$alkyl, nitro, mercapto, $(C_1-C_4)$alkylthio, halo and $(C_1-C_4)$alkoxy. "Substituted alkyl" means one or more of the hydrogens on the carbon chain are replaced by another substituent, such as cyano, hydroxy, $(C_1-C_4)$alkyl, nitro, mercapto, $(C_1-C_4)$alkylthio, halo, carbonyl and $(C_1-C_4)$alkoxy. "Substituted aralkyl" means one or more hydrogens on the aromatic ring or alkyl chain are replaced by another substituent, such as cyano, hydroxy, $(C_1-C_4)$ alkyl, nitro, mercapto, $(C_1-C_4)$alkylthio, halo, carbonyl and $(C_1-C_4)$alkoxy.

"Iminating agent" refers to any compound that reacts with an aldehyde to form an amine. "Aldehyde" refers to aldehydes and aldehyde derivatives, such as acetals and hemiacetals. "Halogenating agent" refers to any material that reacts with a formimine to produce a haloformimine.

All amounts are percent by weight ("% wt"), unless otherwise noted. All ranges are inclusive. As used throughout the specification, the following abbreviations are applied: g=gram; C=Centigrade; mL=milliliter; m.p.=melting point; and mol=mole.

The process of the present invention may be used to prepare the haloformimine compounds of formula (I). It is preferred that at least one of X and Y is bromine or chlorine. It is more preferred that the haloformimines are those wherein R=$OR^2$. When any of $R^1$, $R^2$, $R^3$, $R^4$, $R^5$, $R^6$, $R^7$, $R^8$ and $R^9$ are alkyl or substituted alkyl, it is preferred that they are $(C_1-C_8)$alkyl or substituted $(C_1-C_8)$alkyl. When R is N=$CR^5R^6$, it is preferred that at least one of $R^5$ and $R^6$ is bromine or chlorine.

Suitable haloformimine compounds that can be prepared by the process of the present invention include, but are not limited to: bromochloroformaldoxime; dibromoformaldoxime; dichloroformaldoxime; 2-chloro-2-hydroxyimino acetic acid; 2-chloro-2-hydroxyimino methyl acetate; 2-chloro-2-(acetoxyimino) ethyl acetate; 2-bromo-2-hydroxyimino ethyl acetate; 2-chloro-2-(acetoxyimino) methyl acetate; 2-chloro-2-(benzoyloxyimino) methyl acetate; 2-chloro-2-(N-methylcarbamoyloxyimino) methyl acetate; 2-chloro-2-hydroxyimino benzyl acetate; 2-bromo-2-hydroxyimino benzyl acetate; 2-chloro-2-hydroxyimino phenyl acetate; 2-bromo-2-hydroxyimino phenyl acetate; 2-chloro-2-hydroxyimino octyl acetate; and 2-bromo-2-hydroxyimino octyl acetate.

The formimine compounds useful in the present invention are any that are capable of reacting with a halogenating agent to give the haloformimine compounds of formula (I). In general, the formimine compounds useful in the present invention are those of formula (II)

(II)

wherein $X^3$ and $X^4$ are independently selected from halogen and hydrogen; $Y^2$=H, $CO^2R^1$, $CX^4$(=NR), $C(O)NR^{10}R^{11}$; R, $R^1$, $R^2$, $R^3$, $R^4$, $R^5$, $R^6$, $R^7$, $R^8$, $R^9$, $R^{10}$, and $R^{11}$ are as defined above; provided that at least one of $X^3$ and $X^4$ is hydrogen. Preferred formimines are those wherein R=$OR^2$.

The formimine compounds useful in the present invention can be prepared by methods well-known in the art. Such methods include the reaction of aldehydes or other carbonyl containing compounds with an iminating agent, such as hydrazine; a substituted hydrazine, such as phenylhydrazine, dimethylhydrazine, and t-butylhydrazine; hydroxylamine; a substituted hydroxylamine, such as methyl hydroxylamine and ethyl hydroxylamine; and hydrazones, such as phenylhydrazone. Monohaloformimines can also be used as formimine compounds in the present invention to prepare dihaloformimines. Such monohaloformimines can be prepared by the process of the present invention or other known methods. For example, Kozikowski et al., *Journal of Organic Chemistry*, vol. 48, pp 366–372 (1983), discloses methods of preparing monohaloformimine compounds, herein incorporated by reference to the extent it teaches how to prepare such compounds.

In the process of the present invention, a sufficient amount of a base is combined with a formimine compound and a solvent to provide a mixture having a pH in the range of 2 to 5. It is preferred that the pH of the mixture is 2.5 to 4.5, and more preferably in the range of 3.0 to 4.0. Any base that does not react with the formimine or deactivate the halogenating agent is useful as a base in the present invention. Suitable bases include, but are not limited to: sodium bicarbonate, potassium bicarbonate, sodium carbonate, potassium carbonate, sodium hydroxide, potassium hydroxide, sodium bisulfate, sodium acetate, potassium acetate, ammonium hydroxide, sodium methoxide, potassium methoxide, sodium ethoxide, potassium ethoxide, and mixtures thereof. It is preferred that the base is not an amine base.

The solvent, formimine compound and base may be combined in any order. Suitable solvents include water, methylene dichloride, chloroform, carbon tetrachloride, methylene dibromide, bromoform, carbon tetrabromide, ethylene dichloride, trichloroethane, tetrachloroethane, ethylene dibromide, toluene, xylene, benzotrifluoride, and mixtures thereof It is preferred that the solvent is water.

Any halogenating agent that is capable of reacting with a formimine compound to provide a haloformimine is useful in the present invention. Suitable halogenating agents include, but are not limited to: chlorine, bromine, iodine, thionyl chloride, sulfuryl chloride, hypochlorous acid, hypobromous acid, sodium hypochlorite, potassium hypochlorite, calcium hypochlorite, sodium hypobromite, potassium hypobromite, calcium hypobromite, N-chlorosuccinimide, N-bromosuccinimide, N-iodosucccinimide, t-butyl hypochlorite, t-butyl hypobromite, and mixed halogens, such as bromine chloride. It is preferred that the halogenating agent is chlorine, bromine, sodium hypochlorite, potassium hypochlorite, calcium hypochlorite, sodium hypobromite, potassium hypobromite, or calcium hypobromite.

When the halogenating agent is a liquid, it may be added to the reaction directly or may be dissolved in a solvent and then added to the reaction. When the halogenating agent is a solid, it is slurried or dissolved in a solvent prior to addition to the reaction. When the halogenating agent is a gas, it may be bubbled through the reaction mixture or may be used to saturate a solvent and then added as a liquid. The solvent used to dissolve the halogenating agent may be the same as, or different from, the solvent combined with the formimine compound and base. Suitable solvents for use with the halogenating agents include, but are not limited to: water, organic solvents and mixtures thereof Suitable organic solvents include, but are not limited to: methylene dichloride, chloroform, carbon tetrachloride, methylene dibromide, bromoform, carbon tetrabromide, ethylene dichloride, trichloroethane, tetrachloroethane, ethylene dibromide, toluene, xylene, benzotrifluoride, and the like. The solvent used with the halogenating agent need not be miscible with the solvent combined with the formimine. It is preferred that the solvent for the halogenating agent is water or methylene dichloride.

The halogenating agent is generally added to the reaction at a rate such that the temperature of the reaction does not rise above 25° C. It is preferred that the halogenating agent be added at a rate such that the temperature of the reaction does not rise above 15° C., and more preferably not above 10° C.

The amount of the halogenating agent useful in the present invention depends upon the formimine compound and the particular halogenating agent used. Typically, the amount of halogenating agent is from 0.25 to 3 mole equivalents, based on the formimine compound, and preferably from 0.5 to 2.0 mole equivalents.

The process of the present invention provides high purity haloformimine compounds in high yields when the pH of the reaction during halogenation is maintained at a pH in the range of 2 to 5. It is preferred that the pH is 2.5 to 4.5, and more preferably in the range of 3.0 to 4.0.

How the pH of the reaction is maintained is not critical to the invention; pH may be maintained by any conventional means. For example, the pH of the reaction may be maintained by the use of a buffer as a base to be combined with the formimine, by the addition of a second base during the course of halogenation or by the use of a basic halogenating agent. Acetate buffer is suitable for use as a base in the present invention. If a second base is added during the halogenation step, the second base may be added continuously or periodically. Any base that maintains the pH of the reaction mixture in the range of 2 to 5, does not deactivate the halogenating agent, and does not react with the formimine or haloformimine produced is suitable for use as a second base in the present invention. Strong bases may be used as the second base in the present invention as long as the reaction mixture is very well mixed and/or the strong base is well diluted. If a second base is used, it is preferred that the second base in the present invention is a weak base. Suitable weak bases are those having a $pK_b$ of 4 to 12, and preferably a $pK_b$ of 5 to 10.

Suitable second bases include, but are not limited to: tetrabutylammonium hydroxide, sodium bicarbonate, potassium bicarbonate, sodium carbonate, potassium carbonate, sodium hydroxide, potassium hydroxide, sodium bisulfate, potassium bisulfate, sodium acetate, potassium acetate, ammonium hydroxide, sodium methoxide, potassium methoxide, sodium ethoxide, potassium ethoxide, trisodium phosphate, tripotassium phosphate, triethylamine, trimethylamine, pyridine, aniline, sodium dihydrogen borate, potassium dihydrogen borate, hypobromous acid, hypochlorous acid, disodium hydrogen phosphate, dipotassium hydrogen phosphate, sodium dihydrogen phosphate, potassium dihydrogen phosphate, sodium hydrogen sulfide, sodium sulfate and mixtures thereof. It is preferred that the second base is sodium bicarbonate, potassium bicarbonate, sodium acetate, potassium acetate, sodium dihydrogen borate, potassium dihydrogen borate, hypobromous acid, hypochlorous acid, disodium hydrogen phosphate, dipotassium hydrogen phosphate, sodium dihydrogen phosphate, potassium dihydrogen phosphate, and sodium sulfate.

The amount of the second base to be added during the halogenation step is that amount necessary to maintain the pH of the reaction mixture in the range of 2 to 5. It is preferred that the amount of the second base be sufficient to maintain the pH in the range of 2.5 and 4.5, more preferably in the range of 3.0 and 4.0.

When the second base is added to the reaction mixture continuously, it may be combined with the halogenating agent prior to addition to the reaction or added simultaneous with, but separate from, the halogenating agent. When the second base is added to the reaction mixture periodically, it should be added before the pH of the reaction mixture falls below 2. It is preferred that the second base be added continuously, and more preferably that the second base and halogenating agent be combined prior to addition to the reaction.

A basic halogenating agent may maintain the pH of the reaction without the need for a second base. Such basic halogenating agents are generally the product of a reaction of a halogenating agent with a base. Any basic halogenating agent that maintains a pH of 2 to 5 during the halogenation reaction is suitable. Suitable basic halogenating agents include, but are not limited to: sodium hypochlorite, potassium hypochlorite, calcium hypochlorite, sodium hypobromite, potassium hypobromite and calcium hypobromite.

The halogenation process of the present invention may be carried out at a wide range of temperatures. In general, halogenation may be performed at a temperature in the range of −10° to 100° C. It is preferred that the temperature of the reaction be in the range of −5° to 65° C., and more preferably in the range of 0° to 35° C.

The haloformimine compounds of the present invention may be isolated from the reaction mixture by any conventional means, such as by filtration or solvent extraction. Any solvent that dissolves the haloformimines may be used to extract them from the reaction mixture. Suitable solvents include, but are not limited to: methylene dichloride, ethylene dichloride, ethylene dibromide, and chloroform.

When the haloformimine compounds produced by the process of the present invention are to be used in the synthesis of microbicides, agricultural pesticides or pharmaceutical agents, they may be used without further purification. When the haloformimines are to be used as industrial bactericides, they may be added to any industrial locus directly or first taken up in a carrier and then added to the industrial locus. Suitable carriers for haloformimines include, but are not limited to: water, organic solvents or mixtures thereof. Suitable organic solvents include, but are not limited to: acetonitrile, ethyl acetate, butyl acetate, toluene, xylene, methanol, ethanol, acetone, methyl ethyl ketone, methyl isobutyl ketone, ethylene glycol, diethylene glycol, propylene glycol, dipropylene glycol, and glycol ethers. Alternatively, the haloformimines may be combined with solid carriers, such as diatomaceous earth, silicas, and the like, and then added to the industrial locus.

Haloformimine bactericides are suitable for use in a variety of industrial loci, such as, but not limited to: cooling towers; air washers; mineral slurries; pulp and paper processing fluids; paper coatings; swimming pools; spas; adhesives; caulks; mastics; sealants; agriculture adjuvant preservation; construction products; cosmetics and toiletries; shampoos; disinfectants and antiseptics; formulated industrial and consumer products; soaps; laundry rinse waters; leather and leather products; wood, including lumber, timber, fiberboard, plywood, and wood composites; plastics; lubricants; hydraulic fluids; medical devices; metalworking fluids; emulsions and dispersions; paints, including marine paints; varnishes, including marine varnishes; latexes; odor control fluids; coatings, including marine coatings; petroleum processing fluids; fuel; oil field fluids; photographic chemicals; printing fluids; sanitizers; detergents; textiles, such as fibers; and textile products, such as clothes and carpets.

The amount of haloformimine compounds useful to control bacteria are well known to those skilled in the art and depends upon the locus to be protected and the efficacy of the particular haloformimine compound. The amount of haloformimine compounds suitable to inhibit the growth of bacteria is generally between 0.05 and 5,000 ppm, based on the weight or volume of the locus to be protected.

The following examples are presented to illustrate further various aspects of the present invention, but are not intended to limit the scope of the invention in any aspect.

EXAMPLE 1

This Example demonstrates the process of the present invention using a solvent mixture of water and methylene dichloride.

To a 5000 mL jacketed 3-necked round bottom flask equipped with a bottom take-off valve, a thermocouple, a mechanical stirrer and a condenser were added a 50% solution of glyoxylic acid in water (296.16 g, 2.00 mol) and water (740 mL). To the stirred solution was added a solution of hydroxylamine sulfate (164.14 g, 1.00 mol) in water (350 mL). The solution was stirred at room temperature for one hour to give a formimine compound.

Sodium bicarbonate (325.4 g, 3.87 mol) was added from a screw feeder to adjust the pH to 4.0. Methylene dichloride (1500 mL) was added and the solution was cooled to 5° C. with external cooling through the jacket. To the two-phase, well stirred mixture at 5 to 10° C. was added a solution of bromine (639.28 g, 4.00 mol) in methylene dichloride (750 mL) at a rate such that the temperature of the reaction mixture did not rise above 10° C. (about 2.75 hours). During the addition of bromine, additional sodium bicarbonate (203.9 g, 2.43 mol) was added to maintain the pH in the range of 3 to 4. Upon completion of the addition of bromine, the solution was further stirred for 3 hours, while allowing it to warm to ambient temperature, and then the organic layer was separated. The aqueous layer was extracted with methylene dichloride (2×800 mL). The combined organic extracts were dried over $MgSO_4$, filtered and evaporated on the rotary evaporator to yield 348.1 g (85.8% crude yield, 96.4% purity) of a white solid, m.p. 68–70° C. Upon recrystallization from 260 g of hexane, a white crystalline solid, pure dibromoformaldoxime ("DBFO"), was obtained (290.1 g, 71.5% yield); m.p. 70.0–71.6° C. Mass spectral analysis supported the expected structure.

These data show that the process of the present invention provides haloformimine compounds in high yields and high purity when a mixed solvent is used.

EXAMPLE 2

This Example demonstrates the process of the present invention using water as a solvent.

To a 5000 mL jacketed 3-necked round bottom flask equipped with a bottom take-off valve, a thermocouple, a mechanical stirrer and a condenser was added a 50% solution of glyoxylic acid in water (296.16 g, 2.00 mol). To the stirred solution was added a solution of hydroxylamine sulfate (164.14 g, 1.00 mol) in water (350 mL). The solution was stirred at room temperature for one hour to give a formimine.

The solution was adjusted to pH 3.6 with 50% sodium hydroxide (300 g, 3.75 mol). The solution was cooled to 0° C. with external cooling through the jacket, causing it to form a white slurry. Liquid bromine (639.28 g, 4.00 mol) was added at such a rate that the temperature of the reaction mixture did not rise above 7° C. (about 2.75 hours). During the addition of bromine, a 22% solution of potassium bicarbonate in water (1323 g, 2.91 mol) was added to maintain the pH in the range of 3 to 4. Upon completion of the addition of bromine, the solution was further stirred for 3 hours at 5° C. Methylene dichloride (1000 g) was added to dissolve the product and the organic layer was separated. A second extraction with methylene dichloride (1000 g) was carried out. The combined organic extracts were dried over $MgSO_4$, filtered and evaporated on the rotary evaporator to yield 329.8 g (81.3% crude yield, 98.0% purity) of a white solid, m.p. 68–70° C. Upon recrystallization from 250 g of hexane, a white crystalline solid, pure DBFO, was obtained (280.5 g, 69.1 % yield); m.p. 70–72° C.

These data show that the process of the present invention provides haloformimine compounds in high yields and high purity when a single solvent is used.

EXAMPLES 3–7

Example 2 was repeated except that the second base, its amount or the scale of the reaction were varied. The second base solution was an aqueous solution. These data are reported in Table 1.

TABLE 1

| Example | Glyoxylic Acid (mol) | Second Base Solution | DBFO Purity (%) | DBFO Yield (%) |
|---|---|---|---|---|
| 3 | 2 | 22% $NaHCO_3$ | 99 | 78 |
| 4 | 2 | 22% $NaHCO_3$ | 96 | 83 |
| 5 | 2 | 22% $NaHCO_3$ | 97 | 81 |
| 6 | 0.2 | 15% $KHCO_3$ | 98 | 77 |
| 7 | 0.8 | 22% $KHCO_3$ | 97 | 80 |

The above data show that the process of the invention works with a variety of bases and batch sizes.

EXAMPLE 8

The process of Example 2 was repeated except that the batch size was 0.8 moles of glyoxylic acid, hydroxylamine was used as the iminating agent instead of hydroxylamine sulfate and 15% potassium bicarbonate solution was added as the second base. DBFO was obtained in 77% yield with a purity of 93%.

EXAMPLES 9–11

The process of Example 2 was repeated using sodium hydroxide as the second base. The second base solution was an aqueous solution. The results are reported in Table 2.

TABLE 2

| Example | Glyoxylic Acid (mol) | Second Base Solution | DBFO Purity (%) | DBFO Yield (%) |
|---|---|---|---|---|
| 9 | 2 | 50% NaOH | 74 | 44 |
| 10 | 0.8 | 50% NaOH | 86 | 45 |
| 11 | 0.8 | 25% NaOH | 89 | 56 |

The above data demonstrate that when strong bases are diluted and used as second bases in the present invention, they provide improved yields of haloformimines over known methods.

EXAMPLE 12 (Comparative)

This Example demonstrates the preparation of dibromoformaldoxime according to U.S. Pat. No. 4,879,314 (Hsu).

To a mechanically stirred solution of glyoxylic acid (1.0 mol) in water (600 mL) was added hydroxylamine hydrochloride (69.49 g, 1.0 mol). The solution was stirred at room temperature for 24 hours. Sodium bicarbonate (175 g, 2.08 mol) was added and carefully followed by methylene dichloride (750 mL). To the two-phase, well stirred mixture at 5 to 10° C. was added a solution of bromine (240 g, 1.5 mol) in methylene dichloride (375 mL) at a rate such that the temperature of the reaction mixture did not rise above 10° C. Upon completion of the addition of bromine, the solution was further stirred for 3 hours, cooled, and the organic layer separated. The aqueous layer was extracted with methylene dichloride (2×400 mL). The combined organic extracts were dried over $MgSO_4$, filtered and evaporated to give 82.2 g of DBFO (40.5 % yield). Recrystallization from hexane gave 58.0 g of DBFO (28.6 % yield).

Comparison of the results of example 12 with examples 1 to 8 indicate that the previously known method of preparing haloformimine compounds produces low yields with relatively high levels of by-products or impurities, whereas the process of the present invention results in high yields of haloformimine compounds in high purity.

What is claimed is:

1. A process for preparing haloformimines of the formula

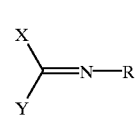

(I)

wherein:

X, $X^1$=halo;

Y=halo, $CO_2R^1$, $CX^1(=NR)$, $C(O)NR^{10}R^{11}$;

R=$OR^2$, $NR^3R^4$, N=$CR^5R^6$;

$R^2$=H, $C(O)R^7$, $(C_1-C_{18})$alkyl, substituted $(C_1-C_{18})$alkyl, $(C_7-C_{10})$aralkyl, substituted $(C_7-C_{10})$aralkyl, phenyl, substituted phenyl;

$R^3$ and $R^4$ are independently selected from: $(C_1-C_{18})$alkyl, substituted $(C_1-C_{18})$alkyl, $(C_7-C_{10})$aralkyl, substituted $(C_7-C_{10})$aralkyl, phenyl, substituted phenyl;

$R^5$ and $R^6$ are independently selected from: H, halo, $CO_2R^1$, $(C_1-C_{18})$alkyl, substituted $(C_1-C_{18})$alkyl, $(C_7-C_{10})$aralkyl, substituted $(C_7-C_{10})$aralkyl, phenyl, substituted phenyl;

$R^7$=$(C_1-C_{18})$alkyl, substituted $(C_1-C_{18})$alkyl, $(C_7-C_{10})$aralkyl, substituted $(C_7-C_{10})$aralkyl, phenyl, substituted phenyl, $NR^8R^9$;

$R^1$, $R^8$, $R^9$, $R^{10}$ and $R^{11}$ are independently selected from: H, ($C_1$–$C_{18}$)alkyl, substituted ($C_1$–$C_{18}$)alkyl, ($C_7$–$C_{10}$)aralkyl, substituted ($C_7$–$C_{10}$)aralkyl, phenyl, substituted phenyl;

wherein the process comprises combining a formimine compound with a solvent and sufficient base to provide a mixture having a pH in the range of 2 to 5, followed by reacting said formimine mixture with a halogenating agent to produce a haloformimine compound, while maintaining the pH of the mixture in the range of 2 to 5.

2. The process according to claim 1 wherein the halogenating agent comprises chlorine, bromine, iodine, thionyl chloride, sulfuryl chloride, hypochlorous acid, hypobromous acid, sodium hypochlorite, potassium hypochlorite, calcium hypochlorite, sodium hypobromite, potassium hypobromite, calcium hypobromite, N-chlorosuccinimide, N-bromosuccinimide, N-iodosuccinimide, t-butyl hypochlorite, t-butyl hypobromite, or mixed halogens.

3. The process of claim 1 wherein at least one of X and Y are selected from the group consisting of bromine and chlorine.

4. The process of claim 3 wherein R is $OR^2$.

5. The process of claim 1 wherein the haloformimine compound comprises bromochloroformaldoxime; dibromoformaldoxime; dichloroformaldoxime; 2-chloro-2-hydroxyimino acetic acid; 2-chloro-2-hydroxyimino methyl acetate; 2-chloro-2-(acetoxyimino) ethyl acetate; 2-bromo-2-hydroxyimino ethyl acetate; 2-chloro-2-(acetoxyimino) methyl acetate; 2-chloro-2-(benzoyloxyimino) methyl acetate; 2-chloro-2-(N-methylcarbamoyloxyimino) methyl acetate; 2-chloro-2-hydroxyimino benzyl acetate; 2-bromo-2-hydroxyimino benzyl acetate; 2-chloro-2-hydroxyimino phenyl acetate; 2-bromo-2-hydroxyimino phenyl acetate; 2-chloro-2-hydroxyimino octyl acetate; or 2-bromo-2-hydroxyimino octyl acetate.

6. The process of claim 1 wherein the amount of the halogenating agent is 0.25 to 3 mole equivalents, based on the formimine compound.

7. The process of claim 1 wherein the pH of the reaction is maintained by continuous or periodic addition of a second base.

8. The process of claim 7 wherein the second base comprises tetrabutylammonium hydroxide, sodium bicarbonate, potassium bicarbonate, sodium carbonate, potassium carbonate, sodium hydroxide, potassium hydroxide, sodium bisulfate, potassium bisulfate, sodium acetate, potassium acetate, ammonium hydroxide, sodium methoxide, potassium methoxide, sodium ethoxide, potassium ethoxide, trisodium phosphate, tripotassium phosphate, triethylamine, trimethylamine, pyridine, aniline, sodium dihydrogen borate, potassium dihydrogen borate, hypobromous acid, hypochlorous acid, disodium hydrogen phosphate, dipotassium hydrogen phosphate, sodium dihydrogen phosphate, potassium dihydrogen phosphate, sodium hydrogen sulfide, sodium sulfate or mixtures thereof.

9. The process of claim 1 wherein the pH of the reaction is maintained in the range of 2.5 to 4.5.

* * * * *